United States Patent [19]

McPherson

[11] Patent Number: 4,994,061
[45] Date of Patent: Feb. 19, 1991

[54] HAIR GRASPING DEVICE

[75] Inventor: Bruce McPherson, Maitland, Fla.

[73] Assignee: Selvac Corporation, Dresher, Pa.

[21] Appl. No.: 319,610

[22] Filed: Mar. 6, 1989

[51] Int. Cl.⁵ .............................................. A61B 17/41
[52] U.S. Cl. ..................................... 606/43; 606/133; 606/210
[58] Field of Search ..................... 128/303.13, 303.17, 128/321, 322, 354, 355; 219/230; 606/43, 133, 206, 210; 81/484, 487, 491

[56] References Cited

U.S. PATENT DOCUMENTS

| | | | |
|---|---|---|---|
| D. 283,543 | 4/1986 | Nakamoto | D24/27 |
| D. 297,261 | 8/1988 | Blake, III et al. | D24/27 |
| 1,301,185 | 4/1919 | Sorensen . | |
| 1,785,919 | 12/1930 | Stickel et al. | 128/354 |
| 2,011,169 | 8/1935 | Wappler | 174/89 |
| 2,373,872 | 4/1945 | Couture | 294/50.9 |
| 2,529,270 | 11/1950 | Webster | 173/273 |
| 2,706,922 | 4/1955 | Allen | 81/85 |
| 3,372,477 | 3/1968 | Hoppe | 30/124 |
| 3,651,811 | 3/1972 | Hildebrandt et al. | 128/303.17 |
| 3,982,542 | 9/1976 | Ford et al. | 128/303.14 |
| 4,001,679 | 1/1977 | Cargile et al. | 324/72.5 |
| 4,033,350 | 7/1977 | Hoshi | 128/303.13 |
| 4,078,569 | 3/1978 | Hoshi | 128/303.13 |
| 4,128,099 | 12/1978 | Bauer | 128/303.17 |
| 4,240,435 | 12/1980 | Yazawa et al. | 128/354 |
| 4,274,413 | 6/1981 | Hahn et al. | 128/303.13 |
| 4,353,371 | 10/1982 | Cosman | 128/303.17 |
| 4,418,692 | 12/1983 | Guay | 128/303.14 |
| 4,640,279 | 2/1987 | Beard | 128/303.14 |
| 4,657,018 | 4/1987 | Hakky | 128/303.15 |
| 4,716,897 | 1/1988 | Noguchi et al. | 128/303.15 |

FOREIGN PATENT DOCUMENTS 2415263 10/1975 Fed. Rep. of Germany .
1026796 7/1983 U.S.S.R. .

Primary Examiner—Lee S. Cohen
Attorney, Agent, or Firm—Panitch, Schwarze Jacobs & Nadel

[57] ABSTRACT

A hair grasping device includes a pair of hair engaging surfaces spring biased to a closed or engaged position in which a hair is grasped therebetween. The device further includes a first clamping member which is slidably disposed with respect to the housing. The first clamping member includes the first hair engaging surface. A spring disposed within the housing biases the first hair engaging surface toward the second hair engaging surface of a second clamping member. High frequency electrical energy is applied to one of the hair engaging surfaces to destroy a grasped hair in the papilla area.

14 Claims, 2 Drawing Sheets

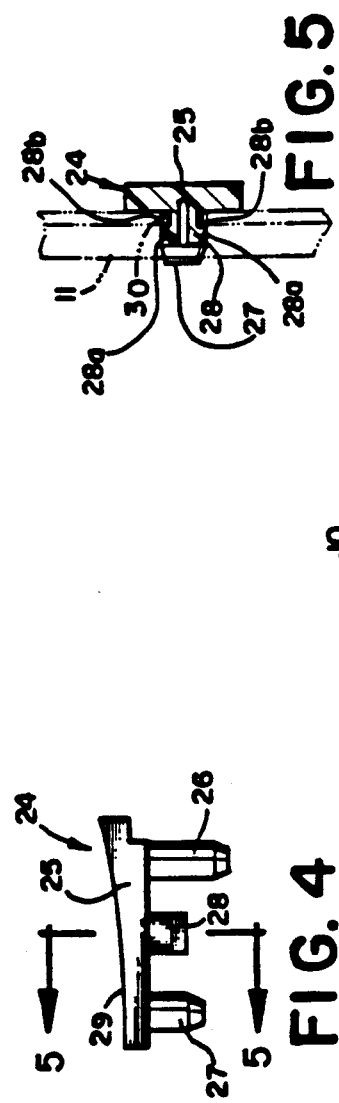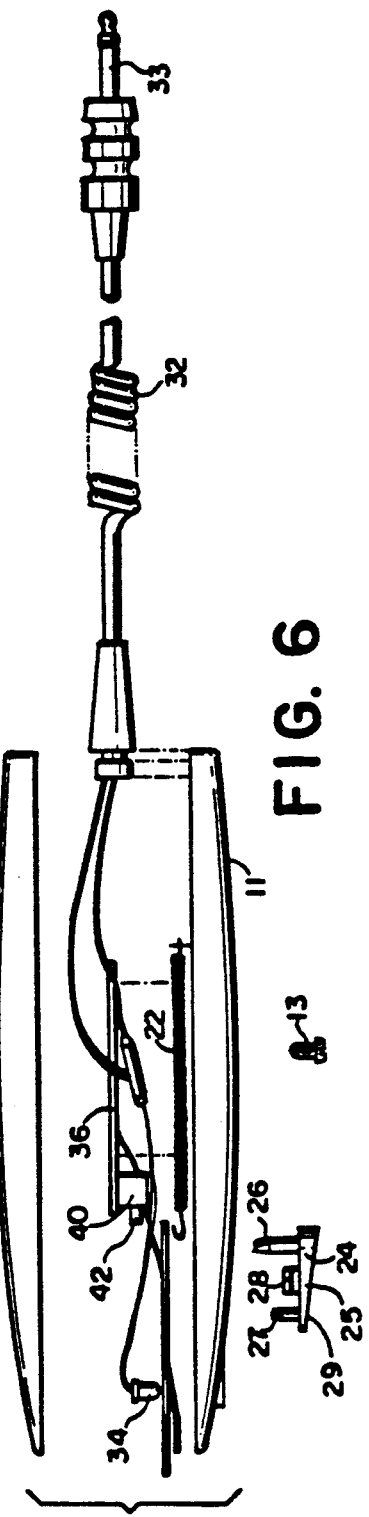

HAIR GRASPING DEVICE

FIELD OF THE INVENTION

The present invention relates to a hair grasping device and, more particularly, to a hair grasping device for holding a hair while high frequency electrical energy is applied thereto.

BACKGROUND OF THE INVENTION

Many different types of devices have been used in an effort to permanently remove unwanted hair. Most of the more recently developed devices used high frequency electricity in an effort to destroy the papilla area at the base of the hair shaft. While these devices have proved effective, they have not all been user friendly.

For instance, in one technique a needle is inserted into the follicle adjacent the hair in an effort to reach the papilla area. High frequency electrical energy is then applied through the needle in an effort to destroy the hair producing papilla area. The more generally used type of such devices has a needle which is used in combination with a tweezer. The drawback of these devices is that the insertion of the needle under the skin produces irritation and swelling, and burning of the tissues.

More recently, hair removal devices use an electrically charged tweezer, which grips the hair at a short distance from the skin. High frequency electrical energy is then directly applied to the hair, wherein the high frequency energy travels down the hair shaft to the papilla area. Since there is no requirement for insertion of a needle into the skin, soreness and irritation of tissue are eliminated. However, this type of device requires more time for hair removal, and, consequently, the user is required to physically compress the tweezers during this time. As such, the user having to firmly grip the tweezers, will eventually become tired, thereby, inhibiting substantial continuous use of the device. In addition, due to the shape of the tweezer grasping end, it is difficult to see the hair the user is trying to grasp. A hair removal device of this type is disclosed in U.S. Pat. No. 4,174,713, which is hereby incorporated by reference.

The present invention overcomes many of the disadvantages inherent in the above-described hair removal devices by providing a hair grasping device which is conducive to continuous use without tiring the operator. The hair grasping device of the present invention is spring biased to a closed position or a position in which a hair is grasped. Consequently, while high frequency electrical energy is applied to the hair, the user does not have to actuate the grasping device. Moreover, use of the present invention is particularly applicable to the elderly or arthritic user who may not be able to put forth the energy necessary to squeeze a pair of tweezers for a considerable length of time.

The hair grasping device embodied in the present invention is adapted to be hand held. More particularly, the hand held device is adapted to be used in either the right or left hand. Moreover, the user can readily view and access the hair to be grasped, thereby preventing the user from becoming frustrated.

SUMMARY OF THE INVENTION

Briefly stated, the present invention comprises a hair grasping device for holding a hair while high frequency electrical energy waves are applied thereto. The device includes a housing having an opening with a first clamping member partially and slidably disposed within the housing and extending through the opening. The first clamping member includes a first hair engaging surface. The device further comprises a second clamping member including a second hair engaging surface. A spring biases the first hair engaging surface toward and into engagement with the second hair engaging surface for grasping a hair therebetween. At least one of the hair engaging surfaces is comprised of an electrically conductive material. A high frequency energy source is electrically connected to the electrically conductive hair engaging surface.

BRIEF DESCRIPTION OF THE DRAWINGS

The foregoing summary, as well as the following detailed description of a preferred embodiment, will be better understood when read in conjunction with the appended drawings. For the purpose of illustrating the invention, there is shown in the drawings an embodiment which is presently preferred, it being understood, however, that the invention is not limited to the specific methods and instrumentalities disclosed. In the drawings:

FIG. 4 is a plan view of a control cap in accordance with the present invention;

FIG. 5 is a cross-sectional view of the control cap of FIG. 4 taken along lines 5—5; and FIG. 6 is a plan and exploded assembly view of the hair grasping device in accordance with the present invention.

DESCRIPTION OF PREFERRED EMBODIMENT

Figure 1:
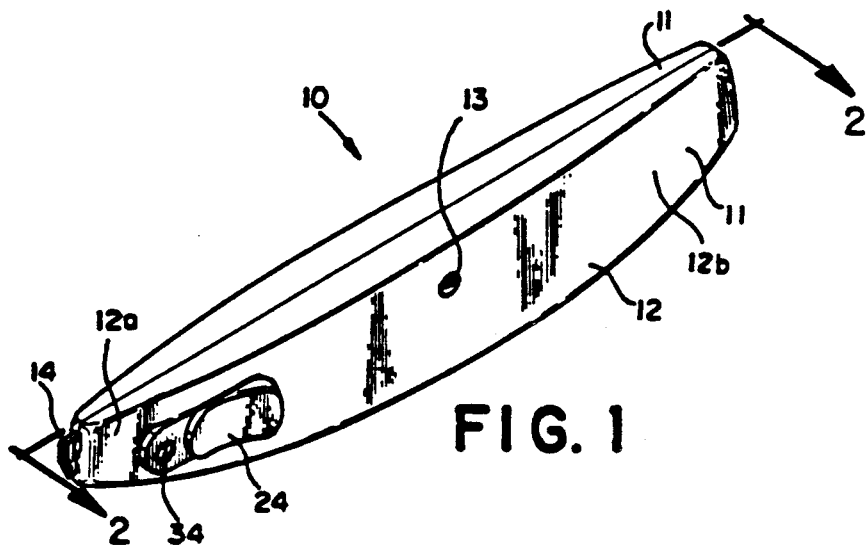
FIG. 1 is a perspective view of a hair grasping device in accordance with the present invention.

Certain terminology is used in the following description for convenience only and should not be considered limiting. For example, the words "right," "left," "lower" and "upper" designate directions in the drawings to which reference is made. The words "inwardly" and "outwardly" refer to directions toward and away from, respectively, the geometric center of the hair grasping device and designated parts thereof. Said terminology includes the words above specifically mentioned, derivatives thereof and words of similar import.

Referring to the drawings in detail, wherein like numerals indicate like elements throughout, there is shown in FIGS. 1 through 6 a preferred embodiment of a hair grasping device in accordance with the present invention.

Referring to FIG. 1, a hair grasping device generally designated 10 is shown. Hair grasping device 10 includes an elongated housing 12 curved or otherwise shaped generally so as to fit comfortably within the hand of a user. Housing 12 includes a first end 12a and a second end 12b. The first end 12a is open. The precise shape of housing 12 has advantages in that it is equally conducive to both right-hand and left-hand use. However, it is within the spirit and scope of the invention to construct housing 12 of any conventional shape conducive to being comfortably hand held, such as the shape of a pocket knife or other such hand held tool or device. In the present embodiment, housing 12 is in the form of two similarly shaped half sections 11 which are constructed of injection-molded, high strength plastic material. Half sections 11 are normally secured together by ultrasonic welding. However, it is also within the spirit and scope of the invention to form housing 12 and/or secure housing half sections 11 together in some other manner.

Figure 2:
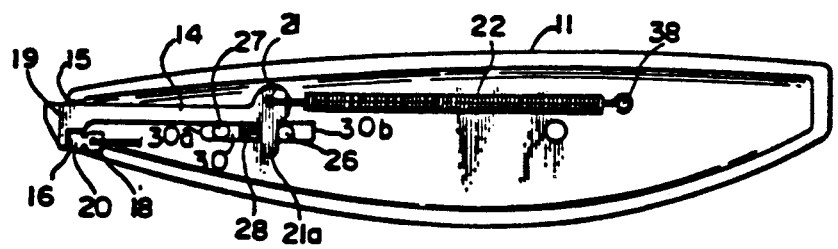
FIG. 2 is a sectional view of the device of FIG. 1 taken along line 2—2 showing the grasping device in a closed position.
Figure 3:
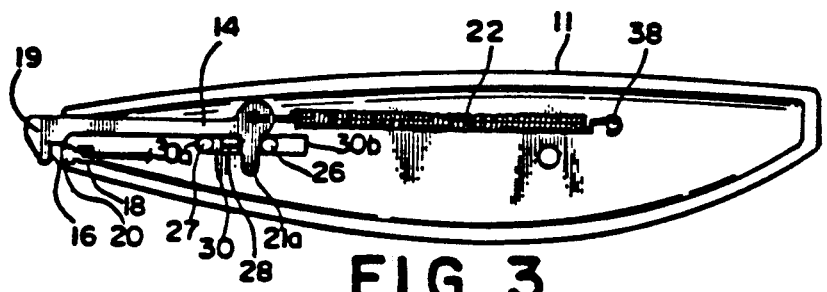
FIG. 3 is a view similar to that of FIG. 2 showing the hair grasping device in an open position.

The interior of housing 12 is shown in FIGS. 2 and 3. Housing 12 includes an opening 15 for slidably receiving a first clamping member 14. Clamping member 14 is disposed through opening 15, such that clamping member 14 is partially and slidably disposed within housing 12. Clamping member 14 includes a generally L-shaped end 19 and opposed thereto a generally P-shaped end 21. Positioned next to L-shaped end 19 adjacent opening 15 is a second clamping member 18. Clamping member 18 is comprised of an electrically conductive material for receiving and applying high frequency electrical energy to a hair disposed between the clamping members 14 and 18. The electrical material of clamping member 18 is preferably a brass alloy or some other material conducive to transmitting high frequency electricity. First clamping member 14 may be made of any non-electrically conductive material such as a high strength plastic material. First and second clamping members 14 and 18 include opposed first and second hair engaging surfaces 16 and 20, respectively, for clamping, engaging or grasping a hair to be removed.

A biasing means, in the present embodiment, a coil spring 22 is employed for biasing the first hair engaging surface 16 into engagement with the second hair engaging surface 20 for grasping a hair (not shown) therebetween. The spring 22 is interconnected between the P-shaped end 21 of first clamping member 14 and a pin 38 fixed on housing 12. The spring 22 is under a predetermined initial tension when the hair engaging surfaces 16 and 20 are in engagement (FIG. 2) to provide the hair engaging surfaces 16 and 20 with sufficient compressive force to firmly grasp and hold the hair to be removed. The magnitude of the grasping or compressive force is sufficient to allow the user to remove a hair by "plucking," without applying high frequency electrical energy. On the other hand, the compressive force does not damage the hair to the point where its electrical conductivity is inhibited.

Slidably disposed on the surface or periphery of housing 12 is an actuating means, in the present embodiment a control cap 24 for actuating the grasping device 10. Housing 12 includes an elongated slot-like aperture 30 wherein control cap 24 is slidably disposed. As shown in FIG. 4, control cap 24 includes a base 25, a projection 26 and a guide pin 27 which extend perpendicular to base 25 into housing 12 through aperture 30.

Control cap 24 further includes a locking member 28 (see FIG. 5) which is snap fitted within elongate aperture 30 for releasably and slidably holding the control cap within aperture 30. The base 25 of control cap 24 is generally oval shaped and greater in size than aperture 30. In the present embodiment, control cap 24 is constructed of high strength plastic material and is normally injection-molded.

Base 25 includes an engagement surface 29 adapted for engagement of a thumb of a user or operator for actuation thereof. In the presently preferred embodiment, engagement surface 29 includes a shallow recess (not shown), generally in the shape of an oval, for enhancing grasping characteristics. Engagement surface 29 may be knurled, roughened or otherwise treated to enhance the grasping characteristics of engagement surface 29.

Locking member 28 is generally U-shaped in cross section and includes a pair of spaced-apart cam-like surfaces 28a positioned at the distal ends thereof with respect to base 25. Cam-like surfaces 28a include shoulders 28b positioned such that a wall of housing 12 fits between shoulders 28b and base 25 (see FIG. 5). To lock control cap 24 within aperture 30, cam-like surfaces 28a are placed against the circumference of aperture 30 with guide pin 27 and projection 26 positioned partially within aperture 30. A force is then applied to control cap 24 along the longitudinal axis of locking member 28, such that cam-like surfaces 28a deflect toward each other until they are positioned close enough to each other to pass through aperture 30. Once cam-like surfaces 28a pass through aperture 30, they deflect away from each other due to their natural resiliency, such that the wall of housing 12 is positioned between shoulders 28b and base 25, to thereby snap, fit or lock control cap 24 within aperture 30.

Elongate aperture 30 has a first end 30a and a second end 30b. The first end 30a of aperture 30 is positioned closer to the first end 12a of housing 12 than the second end 30b of aperture 30. The second end 30b of aperture 30 is positioned closer to the second end 12b of housing 12 than the first end 30a of aperture 30.

When hair engaging surfaces 16 and 20 are interengaged under the bias of spring 20 (FIG. 2), the leg 21a of the P-shaped end of clamp member 14 engages projection 26 of control cap 24, biasing control cap 24 toward the second end 30b of aperture 30. One purpose of guide pin 26 is to limit the movement of control cap 24, which, in turn, limits the movement of hair engaging surfaces 16 and 20. As control cap 24 is moved toward the first end 30a of aperture 30, the first clamping member 14 correspondingly moves away from the second clamping member 18 and hair engaging surfaces 16 and 20 begin to separate with respect to each other. When guide pin 27 engages first end 30a of aperture 30, hair engaging surfaces 16 and 20 are at a point of maximum separation (see FIG. 3). At this point of maximum separation, hair engaging surfaces 16 and 20 are sufficiently spaced to allow the user to readily view and access the hair to be removed, thereby preventing user frustration. On the other hand, when control cap 24 is moved towards second end 30b of aperture 30, hair engaging surface 16 moves toward hair engaging surface 20 under the bias of spring 22 until both surfaces 16 and 20 engage (see FIG. 2). Unlike guide pin 27, projection 26 does not engage second end 30b of aperture 30 because the length of clamping member 14 is such that when both hair engaging surfaces come into contact, P-shaped end 21 and projection 27 fall short of second end 30b.

When control cap 24 is positioned proximate the second end 30b of aperture 30, the hair engaging surfaces 16 and 20 are in contact with each other, or in a closed position as shown in FIG. 2. When the control cap 24 is moved toward the first end 30a of aperture 30, the hair engaging surfaces disengage and are in an open position as shown in FIG. 3. Thus, the position of control cap 24 corresponds to the position of first clamping member 14 and the relative position of hair engaging surfaces 16 and 20.

Referring now to FIG. 6, hair grasping device 10 is connected to an electrical source (not shown) of high frequency electrical energy through a coaxial cable 32 having a connector end 33. Cable 32 includes a casing which is constructed of insulative material such as nylon, or any other non-conductive material. Housing 12 secures coaxial cable 32 therewithin between half sections 11 in a grommet-like manner. Coaxial cable 32 includes two voltage wires which are electrically interconnected between a switch assembly 36 disposed within housing 12 and connector end 33. Housing 12 further includes a removable plug 13 which permits access to switch assembly 36. That is, after hair grasping device 10 is assembled, plug 13 can be removed to allow the antenna (not shown) of switch assembly 36 to be adjusted so that switch assembly 36 can be fine tuned after assembly.

Switch assembly 36 includes a switch element 40 for activating the switch assembly. Switch element 40 has a spring biased actuating member 42. Actuating member 42 is spring biased towards the first end 30a such that when the hair engaging surfaces 16 and 20 are engaged, projection 26 is clamped between leg 21a and actuating member 42. Projection 26 is of sufficient length to engage actuating member 42 upon sliding control cap 24 towards second end 30b. When actuating member 42 is depressed by projection 26, a cycle begins wherein high frequency electrical energy emanates from hair engaging surface 20 for a period of time which can be adjusted at the electrical source. The remaining portions of switch assembly 36 are of conventional structure and, accordingly, their details do not form any part of the instant invention.

In use, the user or operator slides control cap 24 towards light 34 to place the hair engaging surfaces 16 and 20 in an open or separated position (see FIG. 3). The operator then presses the hair grasping device down against the skin with hair engaging surfaces 16 and 20 positioned about the hair to be removed. The second hair engaging surface 20 is positioned within the housing 12 so that a small space is provided between hair engaging surface 20 and the skin of the user. Control cap 24 is then released and the biasing action of spring 22 brings hair engaging surfaces 16 and 20 into engagement with the hair, thereby grasping and holding the hair therebetween. The user then slides control cap 24 towards the second end 30b of aperture 30 until projection 26 separates from leg 21a and engages actuation member 42. The user continues to slide control cap 24 until actuation member 42 is depressed to the point where switch assembly 36 is activated. Light 34 illuminates upon the activation of switch assembly 36, and remains illuminated until the cycle time has expired. That is, upon control cap 24 actuating switch element 40, switch assembly 36 begins the hair removal process by applying high frequency electrical energy to the hair which is transmitted to the papilla area of the hair in the manner described in detail in the above-referenced U.S. Pat. No. 4,174,713. When light 34 is no longer illuminated the user knows the cycle time has expired and the hair can be pulled out. To remove the hair from between hair engaging surfaces 16 and 20, the operator again slides control cap 24 towards light 34 against the biasing action of spring 22 to separate hair engaging surfaces 16 and 20.

From the foregoing description, it can be seen that the present invention comprises a hair grasping device which is biased into a hair grasping or closed position, thereby being conducive to continuous use without tiring the operator. It will be recognized by those skilled in the art that changes may be made to the above-described described embodiment of the invention without departing from the broad inventive concepts thereof. For example, the device 10 may be used for removal of hair without the application of high frequency energy (i.e., plucking). It is understood, therefore, that this invention is not limited to the particular embodiments disclosed, but is intended to cover all modifications which are within the spirit and scope of the invention as defined by the appended claims.

I claim:

1. A hair grasping device for hair removal comprising:
    a housing;
    a first clamping member slidably disposed with respect to said housing and including a first hair engaging surface;
    a second clamping member including a second hair engaging surface;
    a biasing means for biasing the first clamping member toward the second clamping member and said first hair engaging surface into engagement with said second hair engaging surface for grasping and holding a hair therebetween; and
    a control cap slidably disposed on the periphery of said housing, said cap including a projection extending into said housing through an aperture thereof, said projection engaging said first clamping member for movement of said first clamping member against the bias of said biasing means such that the position of said hair engaging surfaces with respect to each other is dependent upon the position of said control cap.

2. A hair grasping device as recited in claim 1 wherein said second hair engaging surface is secured to said housing.

3. The hair grasping device as recited in claim 2 wherein said biasing means is a spring interconnected between said first clamping member and said housing.

4. The hair grasping device as recited in claim 2 wherein said first clamping member is generally L-shaped.

5. The hair grasping device as recited in claim 2 wherein at least one of said hair engaging surfaces comprise an electrically conductive material.

6. The hair grasping device as recited in claim 5 and further including a high frequency energy source means for applying high frequency electrical energy to said one conductive hair engaging surface.

7. The hair grasping device as recited in claim 6 wherein said housing aperture is generally elongate.

8. A hair grasping device for grasping and holding a hair while high frequency electrical energy is applied thereto, said device comprising:
    a housing including an opening;
    a first clamping member partially and slidably disposed within said housing, said first clamping member further being disposed through said opening and including a first hair engaging surface outside of the housing;
    a second clamping member including a second hair engaging surface;
    a biasing means for biasing the first clamping member toward the second clamping member and said first hair engaging surface toward and into engagement with said second hair engaging surface for grasping and holding a hair therebetween, at least one of said hair engaging surfaces being comprised of an electrically conductive material;

a control cap slidably disposed on the periphery of said housing, said cap including a projection extending into said housing through an aperture thereof, said projection being in engagement with said first clamping member for movement of said first clamping member against the bias of said biasing means such that the position of said hair engaging surfaces with respect to each other is dependent upon the position of said control cap; and a high frequency energy source electrically connected to said conductive hair engaging surface for providing high frequency electrical energy to said one conductive hair engaging surface.

9. The hair grasping device as recited in claim 8 wherein said second hair engaging surface is secured to said housing adjacent said first clamping member.

10. The hair grasping device as recited in claim 8 wherein said biasing means is a spring interconnected between said first clamping member and said housing.

11. The hair grasping device as recited in claim 8 wherein said housing aperture is generally elongate.

12. The hair grasping device as recited in claim 8 wherein said first clamping member is generally L-shaped.

13. A hair grasping device for grasping and holding a hair while high frequency electrical energy is applied thereto, said device comprising:

a generally elongated housing having a first and a second end, said first end being open;

a first generally L-shaped clamping member partially and slidably disposed within said housing, said L-shaped clamping member further being disposed through said opening and including a first hair engaging surface outside said housing;

a second clamping member positioned adjacent said L-shaped clamping member and including a second hair engaging surface;

a spring interconnected between said L-shaped clamping member and said housing for biasing said L-shaped clamping member toward said second end of said housing and for biasing said first hair engaging surface toward and into engagement with said second hair engaging surface; and a control cap slidably disposed on the periphery of said housing, said cap including a projection extending into said housing through an elongate aperture in said housing, said projection engaging said L-shaped member for moving the L-shaped member against the bias of the spring such that the position of said hair engaging surfaces with respect to each other is determined by the position of said control cap with respect to said housing.

14. The hair grasping device as recited in claim 17 wherein said elongate aperture has a first end and a second end, said first end of said aperture being positioned closer to said first end of said housing than said second end of said aperture and said second end of said aperture being positioned closer to said second end of said housing than said first end of said aperture, said control cap projection engaging said L-shaped member such that said spring biases said control cap towards said second end of said aperture, whereby when said control cap is positioned proximate said second end of said aperture said hair engaging surfaces are in contact with each other and when said control cap is moved toward said first end of said aperture said hair engaging surfaces are disengaged.

* * * * *